United States Patent [19]
Dobna et al.

[11] 4,362,621
[45] Dec. 7, 1982

[54] RADIAL FLOW CELL

[75] Inventors: Robert W. Dobna, Rahway; B. Allen Mayles, Manalapan; Thomas H. Stoudt, Westfield, all of N.J.

[73] Assignee: Merck & Co., Inc., Rahway, N.J.

[21] Appl. No.: 258,109

[22] Filed: Apr. 27, 1981

[51] Int. Cl.³ .................................. B01D 35/22
[52] U.S. Cl. ........................ 210/450; 210/456; 210/650
[58] Field of Search .......... 210/450, 456, 451, 321.1, 210/489, 650, 651

[56] References Cited

U.S. PATENT DOCUMENTS 3,930,990  1/1976  Brun et al. .............. 210/651 X
4,159,954  7/1979  Gangemi .................. 210/489 X

OTHER PUBLICATIONS

Nuclepore Filtration Products for the Laboratory, Catalog LAB 40.

*Primary Examiner*—John Adee
*Attorney, Agent, or Firm*—Thomas E. Arther; Mario A. Monaco

[57] ABSTRACT

An improved radial flow cell, comprising two or more sets of inlet port-groove-dam devices for improving the efficiency of radial flows and an efficient filtration device consisting of a micropore membrane and a steel screen support of low retention volume, is useful for aseptic and continuous in-line filtration of heterogeneous mixtures containing high concentrations of solids especially those resulting from fermentation processes.

2 Claims, 7 Drawing Figures

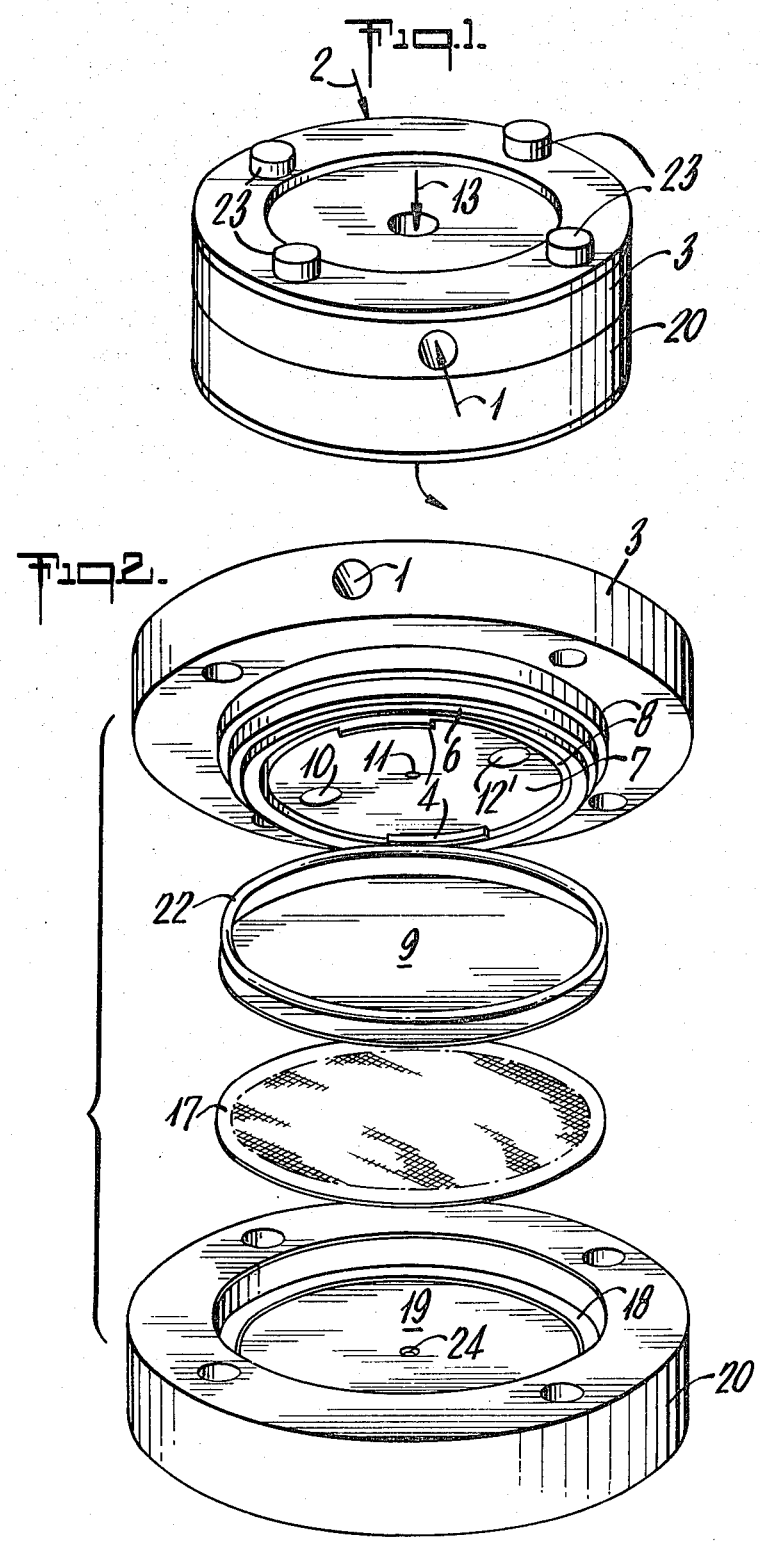

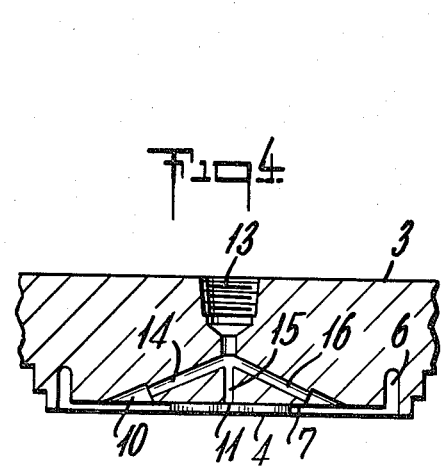
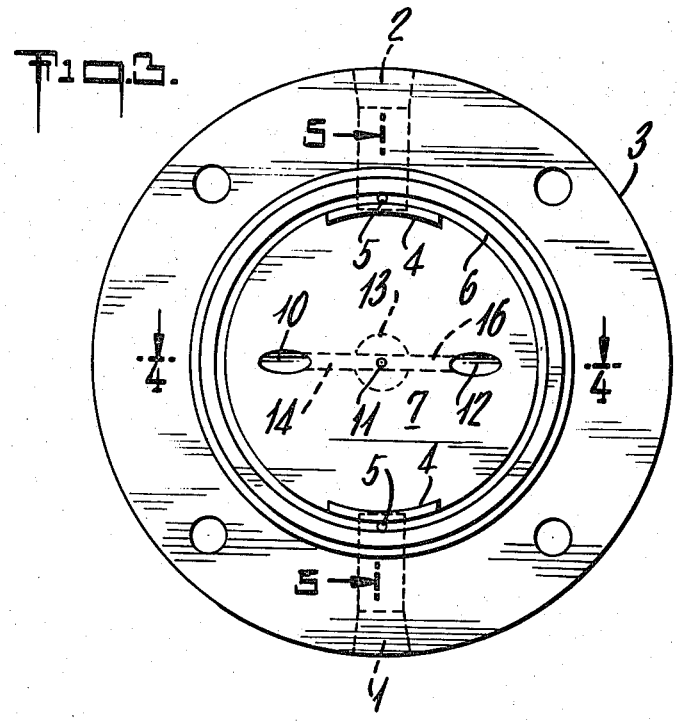
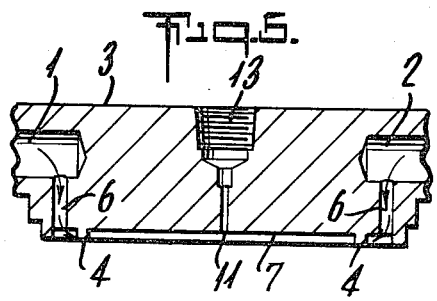
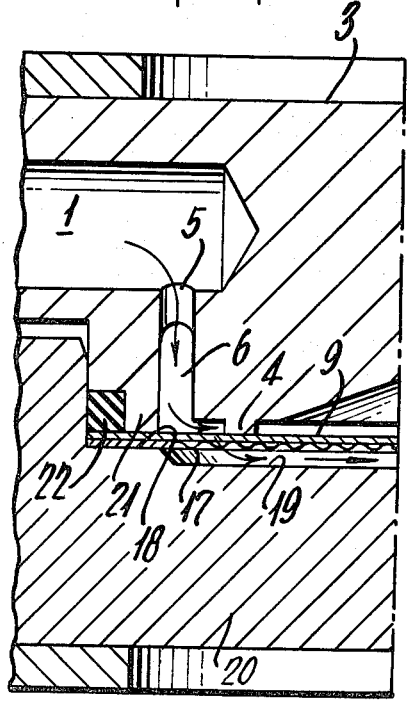

RADIAL FLOW CELL

BACKGROUND OF THE INVENTION

Conventionally, the method of sampling industrial reaction vessels such as fermentors, involves the aseptic and manual removal of individual aliquots through a sample port connected to the vessel into a receiver most commonly a test tube or a flask. As it is essential to obtain representative samples, heterogeneous material must be taken directly from the stirring reaction mixture for sampling. The heterogeneous material which is difficult to filter either due to high viscosity or complexity of constituents of different sizes and textures, usually can only be removed efficiently by the manual method. A notorious example is fermentation broths with unusually high percent solids which are routinely removed aseptically and manually into a receiver protected from contamination only by a cotton plug. The individual samples are subsequently measured, filtered/centrifuged and stored until required analysis can be performed.

The conventional method is inherently unsatisfactory because (1) replacement of receivers for obtaining consecutive samples for analysis is a high contamination risk; (2) the necessary delay incurred during the course of the conventional method, i.e., the time-consuming manual removal, separate filtration, storage prior to analysis, and subsequent manual dilution of samples, are sources of inaccuracy. The delayed analysis may not correspond to the course of the fermentation in real time, and the overly manipulated samples may not give the true analysis of the fermentation due to contamination or decomposition; and (3) total on-line automation and control of the process is impossible with manual sampling.

Automation of an industrial fermentation process highly economize the production by avoiding "over-fermentation". It saves time and energy. It also eliminates the risk of "spoiling" the fermentation where sensitive products are involved and may decompose if the fermentation is not terminated timely.

Most semi-automated biochemical processes, for example, a fermentation process, involve an off-line autoanalyzer which analyzes samples while monitoring the progress of the reaction. However, samples continuously taken from the reaction mixture for sampling must be properly filtered or centrifuged and diluted before entering the autoanalyzer in order to bring the concentrations of analyzed components within the range of the STDS and to avoid clogging of the instrument.

It is well-known how difficult it can be when one attempts to conduct a continuous and efficient filtration of a viscous heterogeneous reaction mixture, especially when it involves high solids containing media and the fermentation lasts for days. Thus, even though some commercially available high-efficiency radial flow-cells have been used for filtering solutions containing extracts or casein from dairy products, no attempts of direct, aseptic, and continuous filtration of a whole fermentation broth has been fully successful.

Accordingly, it is an object of the present invention to provide for an improved flow cell capable of continuous and aseptic filtration for a relatively long period of time a reaction mixture of similar viscosity and complexity of texture as a typical fermentation broth.

Another object of the present invention is to utilize the improved flow cell in a method for automatically monitoring the progress of a reaction which involves (1) filtering a continuous flow of the reaction mixture during the entire reaction period; (2) periodically removing discreet samples from the continuously flowing filtrate stream and feeding them to analyzers in order to monitor the progress of the reaction; (3) returning to the reaction vessel the residue which is swept off from the surface of a biological membrane by a recirculating radial flow of the process stream; and (4) returning to the reaction vessel the unused sterile filtrate.

For example, the present invention could be used to incorporate the automatic monitoring method into a computer-controlled system for the automation of the reaction or the fermentation process.

BRIEF DESCRIPTION OF THE INVENTION

FIG. 1 is a perspective of a preferred embodiment of an assembled radial flow filter according to the invention.

FIG. 2 is an exploded perspective view of the preferred embodiment of a radial flow filter showing each and every part to be assembled according to the invention.

FIG. 3 is a bottom plane view of feeding plate.

FIG. 4 is a cross-sectional view of the feeding plate taken along the line 4—4 of FIG. 3.

FIG. 5 is a cross-sectional view of the feeding plate taken along the line 5—5 of FIG. 3.

FIG. 6 is an enlarged sectional view showing detail of an assembled radial flow filter comprising
 (1) a seal between the feeding plate and the filtrate plate and means by which a membrane is held and supported on the bottom surface of the filtrate plate; and
 (2) an inlet port-groove-dam assembly and paths by which the process stream flow is forced to spread around the dam.

DETAILED DESCRIPTION OF THE INVENTION

Figure 7:
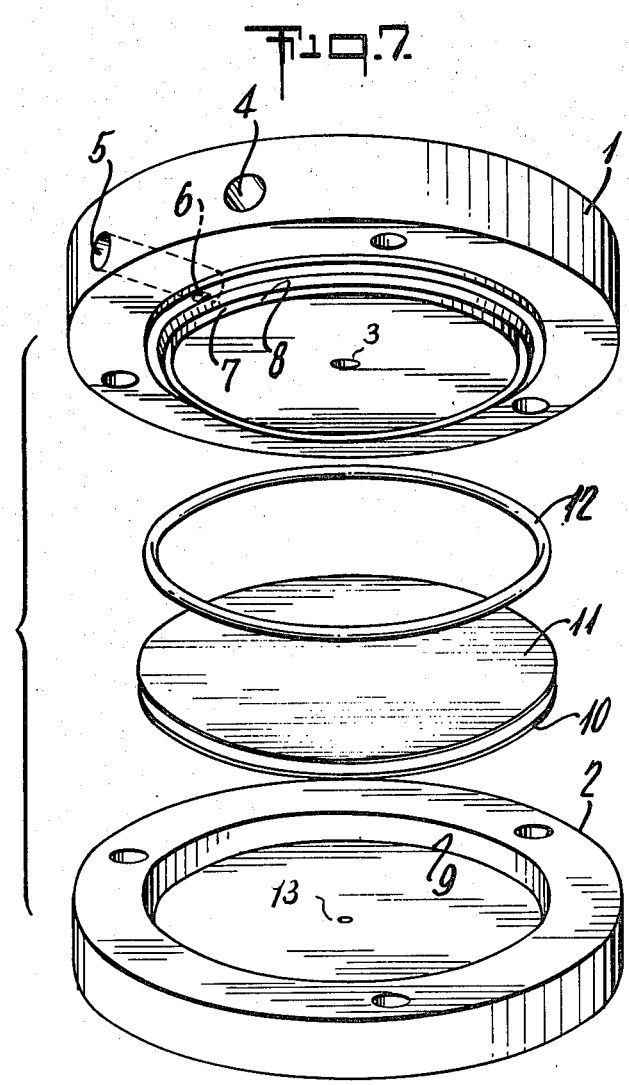
FIG. 7 is an exploded perspective view of the prior art radial flow filter, "Nucleopore Cell".

A. The Prior Art Radial Flow Cell (FIG. 7)

The improved flow cell of the present application is an improvement of the single membrane Nucleopore radial flow cell, hereinafter referred to as "Nucleopore Cell". According to FIG. 7, the Nucleopore Cell consists of a feed plate 1, a filtrate plate 2 and a sealing means i.e., a pressure clamp. The feed plate 1 has an inlet port 4 plus an outlet port 5 for recirculation. In order to generate a radial flow, a first port, be it inlet or outlet, penetrates through the body of the plate until it reaches an opening 3 extending downwardly through the center of the plate, while the second port leads to an orifice 6 at the bottom of a concentric circular groove 7 having a diameter of about ⅔ of the diameter of the plate. The feeding plate has, as an integral part of the plate, a downwardly extending cylindrical portion (the column 8) adapted for engaging sealably with the inner wall of the filtrate plate and sealed thereto by means of an O-ring. Within the column 8, there are located the previously described concentric circular groove 7 and the center-located extended portion of the first port. Both the groove and the first port have their openings facing downwardly at the bottom of the column.

The filtrate plate 2 has a shallow cylindrical cavity 9 adapted for receiving sealably the column of the feeding plate and holds therein the support disc 10 (made of porous polyethylene), the membrane 11 and the O-ring 12. It also has a filtrate output port 13 at the center of its bottom. When assembled together, the column of the top feeding plate is inserted into the cavity of the lower filtrate plate and sealed by means of the O-ring to form the assembled radial flow cell. The sealing is secured by pressing the plates tightly together with an adjustable clamp.

When in use, the process stream is continuously introduced into the assembled flow cell from the inlet port and is to be recirculated in a radial flow across the surface of the membrane thereby sweeping the membrane clean of any residual particles which may block the membrane pores. The particles are concentrated in the process stream while the filtrate passes through the continuously cleansed membrane due to a drop of pressure across the membrane which is partially aided by a pump connected to the filtrate line.

However, in reality when the Nucleopore Cell is used for in-line filtration of heterogeneous materials of texture similar to that of a fermentation broth, only a partial radial flow covering about ⅓ of the membrane surface is generated leaving the rest of the surface subject to gradual blocking. Eventually the residue reached such a level as to hinder the radial flow over the entire membrane surface causing total stoppage of the filtration.

B. The Preferred Embodiment

The improved radial flow cell of the present invention operates substantially in the same manner as the Nucleopore Cell described above but resolves the blocking problem by the following improvements:

I. The efficiency of the radial-flow cleansing function is increased by:
  (1) adding one or more strategically positioned inlet ports, such as ports 1 and 2 of FIG. 1, to the feeding plate 3 so as to generate overlapping radial flows which would cover the entire micropore membrane surface 9 (FIG. 2);
  (2) increasing the number as well as enlarging the openings 10, 11, and 12 (FIGS. 3 and 4) of outlet port 13 at the bottom surface 7 of column 8 to facilitate the exit of the process stream which is concentrated with the residual material swept off the membrane surface 9. This is accomplished by branching the outlet port into three or more branch ports 14, 15, 16 (FIG. 4) each extends downwardly through column 8 and have openings 10, 11, and 12 at the bottom surface of the column. Two of these openings 10 and 12 are enlarged by means of boring through the surface at an angle of about 15°–30°.

II. The efficiency of the filtration is improved by installing a dam 4 (FIG. 2 and FIG. 3) near the orifices 5 at the bottom of the circular groove 6 for the purpose of spreading the incoming process flow to a larger radial area. In order to accomplish this effect, the dams are situated at the periphery of the lower bottom portion 7 of column 8 which constitutes the bottom surface of the feeding plate 3. When the process stream is introduced via the inlet port 1 (FIG. 6), it flows first through the orifice 5 into the circular groove 6 (FIG. 6). Before leaving the groove, a major portion of the stream hits the dam 4 and is forced to spread around the dam. This automatically enlarges the radius of the flow which then sweeps through more than half of the membrane surface 9. Accordingly, a combination of two or more sets of the inlet port-groove-dam device such as shown in FIG. 6, will generate an efficient radial flow capable of sweeping and cleansing the entire surface of the membrane. As a result, the micropore membrane can be used continuously for the entire in-line filtration period without the troublesome blockage.

III. The real time sampling of filtrate has been improved by reducing the filtrate reservoir 19 (FIG. 2) area to insure complete exchange of sample between sampling periods and eliminate timed sample interaction and by replacing the supporting disc in the Nucleopore Cell with a stainless steel screen 17 (FIG. 2) of much larger pores but much less retention volume. The screen is supported by a circular shoulder 18 extending upwardly from the bottom surface 19 (filtrate reservoir) of the cavity of the filtrate plate 20. The screen 17 serves to support the micropore membrane without over retention of filtrate.

Besides the three major improvements described above in I, II, and III, the present invention also includes a modification of the sealing means for joining together the feeding and filter plates. The thickness of the lower outer wall 21 (FIG. 6) flanging the circular groove 6 is increased from about 1/20 cm to about 3/10 cm. The strengthened wall can withstand the sealing pressure exerted by O-ring 22 (FIG. 2), without breakage, for a much longer period of time than the thin (1/20 cm) wall of the Nucleopore Cell. It thus serves the purpose of preventing leakage during continuous in-line filtration which may last for many days.

Finally, to eliminate the bulky and cumbersome clamp, the plates 3 and 20 are secured together by means of nuts 23 (FIG. 1) screwed onto bolts which also provides means for compressing the O-ring seal to make it leak-proof.

In summary, the improved radial flow cell of the present invention, as shown by FIG. 1 and FIG. 2, comprises
  (1) a feeding plate 3 with means for feeding streams of heterogeneous material as described above;
  (2) a filter plate 20 with an outlet port 24 for filtrate, and means for filtration including a screen 17 and a micropore membrane 9; and
  (3) a sealing means which holds the plates together to form the resulting leak-proof radial flow cell.

The following examples illustrate the efficiency of the improved radial flow cell.

EXAMPLE 1

The fermentation broth resulting from a 10 liter fermentation of *S. lactamdurans* in a cerelose medium (see Table I for composition of the medium) for 14 days is filtered through the radial flow cell of the present invention. The following result is obtained:
Effective whole broth flow rates used: 150–1400 ml/min.
Filtrate flow rate achieved: 0.1–0.42 ml/min.
Duration of operation: 14 days. At the time when the filtration is stopped, there is no clogging of the membrane.

TABLE I

| Composition of Cerelose Medium | |
|---|---|
| | Gram per Liter |
| Meat Meal (30 mesh) | 15 |
| Cerelose | 60 |
| DMF | 10 |
| MgSO$_4$.7H$_2$O | 0.5 |

TABLE I-continued

| Composition of Cerelose Medium | |
|---|---|
| | Gram per Liter |
| Glycine | 1.0 |
| P-2000 | 0.25 |
| pH with 25% NaOH | 7.3 |
| Sodium thiosulfate | 1.6 |
| D,L-Lysine.HCl | 0.98 |
| 1,3-diaminopropane | 0.50 |

EXAMPLE 2

The fermentation broth resulting from a 10 liter fermentation of *S. cattleya* in a glycerol medium (see Table II for composition of the medium) for 14 days is filtered through the radial flow cell of the present invention.

The following result is obtained:

Effective whole broth flow rates used: 150–1400 ml/min.

Filtrate flow rate achieved: 0.1–0.42 ml/min.

Duration of operation: 14 days. At the time when the filtration is stopped, there is no clogging of the membrane.

TABLE II

| Composition of Sucrose Medium | |
|---|---|
| | Gram per Liter |
| Glycerol | 20 |
| Distillers solubles | 10 |
| Corn steep liquor | 15 |
| Proflo | 5 |
| $CoCl_2.6H_2O$ | 0.01 |
| Sodium succinate | 1 |
| pH with 50% caustic | 7.5 |

TABLE II-continued

| Composition of Sucrose Medium | |
|---|---|
| | Gram per Liter |
| $CaHPO_4$ | 2.5 |
| P-2000 | 0.25 |

What is claimed is:

1. An improved radial flow cell of the type having
   (a) a feeding plate with means for feeding a heterogeneous broth;
   (b) a filter plate with means for filtration; and
   (c) a sealing means for securing the feeding plate and the filtrate plate together so as to form a leak-proof cell, wherein the improvement comprises means for feeding which further comprises
      (1) two or more circumferentially located inlet ports for feeding a heterogeneous broth;
      (2) a circular groove for receiving via connecting orifices the broth from the inlet ports and thereby generating a radial flow of broth;
      (3) a dam attached to the periphery of the bottom surface of the feeding plate and facing the connecting orifices for enlarging the radius of the radial flow from the circular groove; and
      (4) two or more outlet ports with enlarged openings to facilitate the exit of the concentrated process stream.

2. The radial flow cell of claim 1 wherein the improvement further comprises means for filtration which includes:
   (a) a micropore membrane;
   (b) a screen for supporting the membrane; and
   (c) a circular shoulder extending upwardly from the bottom surface of the cavity of the filter plate for supporting the screen.

* * * * *